United States Patent [19]

Cragoe, Jr. et al.

[11] 3,991,087

[45] Nov. 9, 1976

[54] 8-HALO-11,12-SECOPROSTAGLANDINS

[75] Inventors: Edward J. Cragoe, Jr.; John B. Bicking, both of Lansdale, Pa.

[73] Assignee: Merck & Co., Inc., Rahway, N.J.

[22] Filed: June 6, 1975

[21] Appl. No.: 584,555

Related U.S. Application Data

[63] Continuation-in-part of Ser. No. 424,501, Dec. 13, 1973, abandoned.

[52] U.S. Cl. ............................. 260/408; 260/398; 260/404; 260/404.5; 260/410.9 R; 260/413; 260/417; 260/468 D; 260/535 R; 424/312; 424/314

[51] Int. Cl.$^2$ .................................. C11C 3/00

[58] Field of Search ............... 260/408, 410.9, 413, 260/468 D, 514 D; 424/305, 317, 318

[56] References Cited

UNITED STATES PATENTS

| | | | |
|---|---|---|---|
| 3,718,667 | 2/1973 | Strike et al. | 260/413 |
| 3,759,964 | 9/1973 | Siddall et al. | 260/408 |
| 3,857,831 | 12/1974 | Hayashi et al. | 260/413 |
| 3,862,972 | 1/1975 | Heslinga et al. | 260/413 |
| 3,882,244 | 5/1975 | Lee | 424/318 |

FOREIGN PATENTS OR APPLICATIONS

| | | |
|---|---|---|
| 806,639 | 4/1974 | Belgium |
| 814,089 | 10/1974 | Belgium |

OTHER PUBLICATIONS

Merck Index (1968) pp. 878–879, "Prostaglandins".
Merck Index (1968) pp. 228, 432, Chaulmoogric Acid Esters.

*Primary Examiner*—Helen M. McCarthy
*Attorney, Agent, or Firm*—Thomas E. Arther; Harry E. Westlake, Jr.; Rudolph J. Anderson, Jr.

[57] ABSTRACT

This invention relates to 11,12-secoprostaglandins and processes for their manufacture. These compounds have prostaglandin-like biological activity and are particularly useful as renal vasodilators, for the treatment of hypertension, and for the prevention of thrombus formation.

19 Claims, No Drawings

8-HALO-11,12-SECOPROSTAGLANDINS

RELATIONSHIP TO OTHER APPLICATIONS

This application is a continuation-in-part of copending U.S. application Ser. No. 424,501, filed Dec. 13, 1973, now abandoned.

SUMMARY OF THE INVENTION

This invention relates to novel 11,12-secoprostaglandins. These compounds can be represented by the following structural formula:

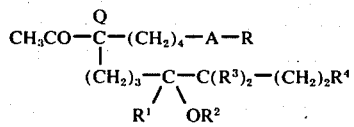

wherein R is selected from the group consisting of carboxy and a carboxy salt being formed from a pharmaceutically acceptable cation, such as metal cations derived from alkali metals, alkaline earth metals, and amines such as ammonia, primary and secondary amines, and quaternary ammonium hydroxides. Especially preferred metal cations are those derived from alkali metals, e.g., sodium, potassium, lithium, and the like, and alkaline earth metals, e.g., calcium, magnesium, and the like, and other metals, i.e., aluminum, iron, and zinc.

Pharmaceutically acceptable cations derived from primary, secondary, or tertiary amines, or quaternary ammonium hydroxides are methylamine, dimethylamine, trimethylamine, ethylamine, N-methylhexylamine, benzylamine, α-phenethylamine, ethylenediamine, piperidine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, tetramethylammonium hydroxide, tetraethylammonium hydroxide, benzyl trimethylammonium and the like.

R is also selected from alkoxycarbonyl (—COOY) wherein Y is alkyl having 1–10 carbon atoms, carbamoyl (—CONH$_2$); substituted carbamoyl (—CONR$^5$R$^6$ wherein R$^5$ and R$^6$ are selected from the group consisting of hydrogen, lower alkyl having 1–4 carbon atoms and diloweralkylaminoalkyl having 4–7 carbon atoms.

A is selected from the group consisting of ethylene (—CH$_2$CH$_2$—), trimethylene (—CH$_2$CH$_2$CH$_2$—), α-methylethylene (—CH$_2$—CH(CH$_3$)—), β-methylethylene (—CH(CH$_3$)CH$_2$—), α,α-dimethylethylene (—CH$_2$—C(CH$_3$)$_2$—), β,β-dimethylethylene (—C(CH$_3$)$_2$CH$_2$—) and oxymethylene (—O—CH$_2$—). (Note that when A consists of a two carbon bridge, the term α refers to the carbon adjacent to R, while β refers to the other carbon atom.)

Q is chloro, bromo, methyl, phenyl, or substituted phenyl.

R$^1$ is independently selected from the group consisting of hydrogen and methyl.

R$^2$ is selected from the group consisting of hydrogen, and lower alkanoyl of 1–5 carbon atoms, e.g., formyl, acetyl, propionyl, butyryl, isobutyryl, valeryl, pivaloyl and the like.

R$^3$ is independently selected from the group consisting of hydrogen and methyl.

R$^4$ is selected from the group consisting of hydrogen, lower alkyl of 1–4 carbon atoms, either straight or branched, (e.g., methyl, ethyl, propyl, isopropyl, butyl, tert-butyl) and 2,2,2-trifluoroethyl. In addition, when R$^4$ is lower alkyl and R$^1$ is methyl, they can be joined together (with abstraction of hydrogen) to form a carbocyclic ring with from 6 to 9 members. Also, when R$^4$ is lower alkyl and R$^1$ is hydrogen, R$^4$ can be joined to the carbon atom bearing R$^1$ and OR$^2$ to form a carbocyclic ring with from 5 to 8 members.

A preferred embodiment of this invention relates to the 11,12-secoprostaglandins having the following general formula:

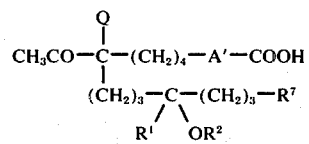

wherein A' is ethylene or oxymethylene;

R$^1$, R$^2$, and Q are as defined above; and R$^7$ is ethyl, isopropyl, or butyl.

It is to be noted that the carbon bearing R$^1$ and OR$^2$ is asymmetric. This invention covers stereoisomers in which this asymmetric center is exclusively in either one or the other of the two possible configurations, R and S. This invention also contemplates that the asymmetric carbon bearing the Q substituent also be prepared in each of its possible configurations.

BACKGROUND OF THE INVENTION

The compounds of formula I are described as 11,12-secoprostaglandins because of their structural relationship to the naturally occurring prostaglandins.

The prostaglandins constitute a biologically prominent class of naturally occurring, highly functionalized C$_{20}$ fatty acids which are anabolized readily in a diverse array of mammalian tissues from three essential fatty acids; namely, 8,11,14-eicosatrienoic acid, 5,8,11,14-eicosatetraenoic acid and 5,8,11,14,17-eicosapentaenoic acid. Each known prostaglandin is a formal derivative of the parent compound, termed "prostanoic acid"; the latter is a C$_{20}$ fatty acid covalently bridged between carbons 8 and 12 such as to form a trans, vicinally-substituted cyclopentane in which the carboxy-bearing side chain is "alpha" or below the plane of the ring and the other side chain is "beta" or above the plane of the ring as depicted in formula III:

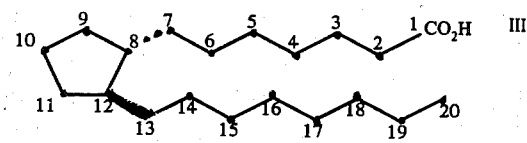

The six known primary prostaglandins, PGE$_1$, PGE$_2$, PGE$_3$, PGF$_{1\alpha}$, PGF$_{2\alpha}$, and PGF$_{3\alpha}$ resulting directly from anabolism of the above cited essential fatty acids via the action of prostaglandin synthetase, as well as the three prostaglandins resulting from in vivo dehydration of the PGE's, i.e., $PGA_1$, $PGA_2$, and $PGA_3$, are divided into three groups; namely, the PGE, PGF, and PGA series on the basis of three distinct cyclopentane nuclear substitution patterns as illustrated as follows:

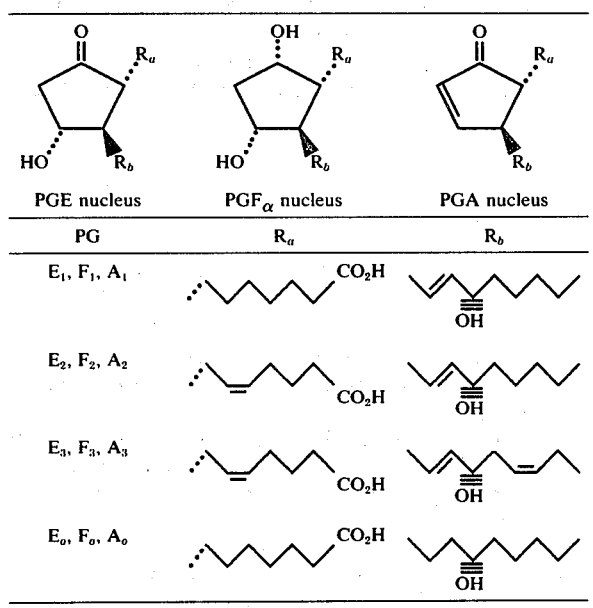

It should be noted that the Arabic subscripts designate the number of carbon-carbon double bonds in the designated compound and that the Greek subscript used in the PGF series designates the sterochemistry of the C–9 hydroxyl group.

Although the prostaglandins were discovered independently in the mid-1930's by Goldblatt [J. Chem. Soc. Chem. Ind. Lond., 52, 1056 (1933)] in England and Von Euler [Arch. Exp. Path. Pharmark., 175, 78 (1934)] in Sweden, these complex natural products received little attention from the scientific community until the early 1960's which coincides with the advent of modern instrumentation (e.g., mass spectrometry) which, in turn, was requisite for their successful isolation and structural elucidation by Bergström and colleagues [see Angew. Chem. Int. Ed., 4, 410 (1965) and references cited therein for an account of this work]. Within the last decade, a massive international scientific effort has been expended in developing both biosynthetic and chemical routes to the prostaglandins and, subsequently, in investigating of their biological activities. During this period, prostaglandins have been shown to occur extensively in low concentrations in a myriad of mammalian tissues where they are both rapidly anabolized and catabolized and to exhibit a vast spectrum of pharmacological activities including prominent roles in (a) functional hyperemia, (b) the inflammatory response, (c) the central nervous system, (d) transport of water and electrolytes, and (e) regulation of cyclic AMP. Further details concerning the prostaglandins can be found in recent reviews of their chemistry [J. E. Pike, Fortschr. Chem. Org. Naturst., 28, 313 (1970) and G. F. Bundy, A. Rep. in Med. Chem., 7, 157 (1972)], biochemistry [J. W. Hinman, A. Rev. Biochem., 41, 161 (1972)], pharmacology [J. R. Weeks, A. Rev. Pharm., 12, 317 (1972)], physiological significance [E. W. Horton, Physiol. Rev., 49, 122 (1969)] and general clinical application [J. W. Hinman, Postgrad. Med. J., 46, 562 (1970)].

The potential application of natural prostaglandins as medicinally useful therapeutic agents in various mammalian disease states is obvious but suffers from three formidable major disadvantages, namely, (a) prostaglandins are known to be rapidly metabolized in vivo in various mammalian tissues to a variety of metabolites which are devoid of the desired original biological activities, (b) the natural prostaglandins are inherently devoid of biological specificity which is requisite for a successful drug, and (c) although limited quantities of prostaglandins are presently produced by both chemical and biochemical processes, their production cost is extremely high; and, consequently, their availability is quite restricted.

Our interest has, therefore, been to synthesize novel compounds structurally related to the natural prostaglandins but with the following unique advantages: (a) simplicity of synthesis leading to low cost of production; (b) specificity of biological activity which may be either of a prostaglandin-mimicking or prostaglandin-antagonizing type; (c) enhanced metabolic stability. The combination of these advantages serves to provide effective, orally and parenterally active therapeutic agents for the treatment of a variety of human and animal diseases. Included are applications in renal, cardiovascular, gastrointestinal, respiratory, and reproductive systems, and in the control of lipid metabolism, inflammation, blood clotting, skin diseases, and certain cancers.

More specifically, in the clinic, prostaglandin agonists can function as agents for improving renal function (e.g., renal vasodilation), antihypertensives, antiulcer agents, agents for fertility control, antithrombotics, antiasthmatics, antilipolytics, antineoplastic agents, and agents for the treatment of certain skin diseases.

Prostaglandin antagonists can function as antiinflammatory agents, anti-diarrheal agents, antipyretics, agents for prevention of premature labor, and agents for the treatment of headache.

The compounds of the present invention are useful as pharmaceutically active compounds. Thus, these compounds are orally active in the treatment of conditions which are responsive to the actions of the natural prostaglandins. It is of course necessary to determine by routine laboratory testing which of the compounds of the present invention are most suitable for a specific end use. Some of the compounds of the invention have prostaglandin-like activity in that they mimic the effect of prostaglandin $E_1$ in stimulating the formation of cyclic AMP in the mouse ovary in vitro.

The compounds of this invention are particularly useful for the treatment of hypertension. Certain of the compounds of the present invention are useful in lowering blood pressure in individuals with blood pressure higher than normal. Thus, for example, the compound 8-acetyl-12-hydroxy-8-phenylheptadecanoic acid is found to be effective in lowering blood pressure in laboratory animals (rats) which have blood pressure higher than that normally observed in such test animals.

Because of their biological activity and ready accessibility, the compounds of the invention are also useful in that they permit large scale animal testing, useful and necessary to understanding of these various disease conditions such as kidney impairment, ulcers, dwarfism caused by poorly-functioning pituitary glands, stroke (thrombus formation), and the like. It will be appreciated that not all of the compounds of this invention have these biological activities to the same degree, but the choice of any particular ones for any given purpose will depend upon several factors including the disease state to be treated.

The compounds of this invention can be administered either topically or systemically, i.e., intravenously, subcutaneously, intramuscularly, orally, rectally, or by aerosolization in the form of sterile implants for long action. They can be formulated in any of a number of pharmaceutical compositions and non-toxic carriers to this end.

The pharmaceutical compositions can be sterile injectable suspensions or solutions, or solid orally administrable pharmaceutically acceptable tablets or capsules; the compositions can also be intended for sublingual administration, or for suppository use. It is especially advantageous to formulate compositions in dosage unit forms for ease and economy of administration and uniformity of dosage. "Dosage unit form" as a term used herein refers to physically discrete units suitable as unitary dosages for animal and human subjects, each unit containing a predetermined quantity of active material calculated to produce the desired biological effect in association with the required pharmaceutical means.

Illustratively, a sterile injectable composition can be in the form of aqueous or oleagenous suspensions or solutions.

The sterile injectable composition can be aqueous or oleagenous suspension or solution. Suspensions can be formulated according to the known art using suitable dispersing and wetting agents and suspending agents. Solutions are similarly prepared from the salt form of the compound. For the laboratory animals, we prefer to use incomplete Freund's adjuvant or sterile saline (9%) as carrier. For human parenteral use, such as intramuscularly, intravenously, or by regional perfusion, the diluent can be a sterile aqueous vehicle containing a preservative; for example, methylparaben, propylparaben, phenol, and chlorobutanol. The aqueous vehicle can also contain sodium chloride, preferably in an amount to be isotonic; as well as a suspending agent, for example, gum arabic, polyvinyl pyrrolidone, methyl cellulose, acetylated monoglyceride (available commercially as Myvacet from Distillation Products Industry, a division of Eastman Kodak Company), monomethyl glyceride, dimethyl glyceride or a moderately high molecular weight polysorbitan (commercially available under the tradenames Tween or Span from Atlas Powder Company, Wilmington, Delaware). Other materials employed in the preparation of chemotherapeutic compositions containing the compound may include glutathione, 1,2-propanediol, glycerol and glucose. Additionally, the pH of the composition is adjusted by use of an aqueous solution such as tris(hydroxymethyl)aminomethane (tris buffer).

Oily pharmaceutical carriers can also be used, since they dissolve the compound and permit high doses. Many oily carriers are commonly employed in pharmaceutical use, such as, for example, mineral oil, lard, cottonseed oil, peanut oil, sesame oil, or the like.

It is preferred to prepare the compositions, whether aqueous or oils, in a concentration in the range of from 2–50 mg./ml. Lower concentrations than 50 mg./mg. are difficult to maintain and are preferably avoided.

Oral administration forms of the drug can also be prepared for laboratory animals or human patients provided that they are encapsulated for delivery in the gut. The drug is subject to enzymatic breakdown in the acid environment of the stomach. The same dosage levels can be used as for injectable forms; however, even higher levels can be used to compensate for biodegradation in the transport. Generally, a solid unit dosage form can be prepared containing from 0.5 mg. to 25 mg. active ingredient.

Whatever the mode of administration, doses in the range of about 0.10 to 20 milligrams per kilogram of body weight administered one to four times per day are used. The exact dose depending on the age, weight, and condition of the patient, and the frequency and route of administration.

The low cost and ready accessibility of the compounds of this invention make them particularly promising for applications in veterinary medicine in which field their utilities are comparable to those in human medicine.

There are a number of inter-related processes useful in preparing the compounds of Formula I. These can all be described as the sub-synthesis of each of the three main moieties of the molecule, i.e., the $(CH_2)_4AR$ chain, the

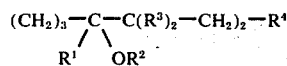

chain, and the Q group which are attached to an asymmetric carbon, and their reaction(s) to form the desired end product.

One major process utilizes as starting materials compounds in which only the Q group is lacking, i.e.,

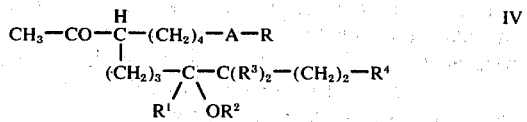

When using these compounds of Formula IV, R is defined to be either a carboxy group or a blocked carboxy group, i.e., a lower alkyl ester wherein lower alkyl is 1–6 carbon atoms. Compounds of this structure are not part of this invention, but are claimed in co-pending U.S. Ser. No. 302,365, filed Oct. 30, 1972, in the names of Cragoe, Bicking and Smith, and in a continuation-in-part application of that application, Ser. No. 389,901, filed Aug. 23, 1973, in the names of the same inventors, both now abandoned.

These starting materials of Formula IV where R is carboxy are reacted with cupric chloride and lithium chloride to yield compounds of Formula I wherein Q is chloro; and with cupric bromide and lithium bromide to yield compounds wherein Q is bromo. When compounds wherein Q is methyl are desired, the compounds of Formula IV where R is blocked carboxy as described above are first treated with molecular bromine. The products of this reaction (Q equals bromo) are reacted with dimethyl copper lithium (generated in situ) to give products of Formula IV where Q is methyl. The carboxyblocking ester function can subsequently be removed by basic hydrolysis.

To prepare compounds of Formula I wherein Q is phenyl, a sequential synthesis of the molecule is employed.

First, the starting material is one of the following reagents:

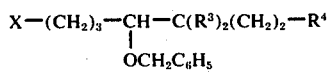
       V or

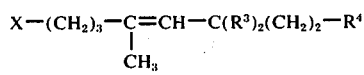
       VI wherein X is halogen, preferably chlorine or bromine, and $R^3$ and $R^4$ are as defined in Formula I.

Reagent V is used to obtain final compounds of Formula I wherein $R^1$ is hydrogen; the reagent VI is used when $R^1$ is methyl in the desired final product.

Either of the desired reagents is reacted with phenyl acetone or a substituted phenyl acetone, viz.,

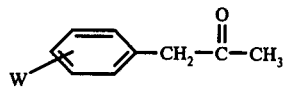
       VII wherein W indicates an optional substituent (or substituents). Substituents which are suitable for halogens, e.g., chlorine, bromine, iodine, or fluorine; lower alkyl, e.g., methyl, ethyl, propyl, butyl, pentyl, hexyl, and the like; lower alkoxy, as methoxy, ethoxy, propoxy, and the like. The substituent(s) can be ortho-, meta-, or para-position, and mono- or poly-substitution can be made. When there is poly-substituent, the substituents need not necessarily be the same.

The reaction between compounds V or VI and VII is conducted in the following manner:

Compound VII is treated with an equivalent of base such as sodium hydride, sodium ethoxide, sodium amide, or the like. The enolate anion thus produced is alkylated by reaction with either compound V or VI. This reaction is conducted in an inert solvent such as dimethylformamide, dimethylformamide:benzene (1:1) or diglyme, at a temperature ranging from 40° to 120° C. The reactants are employed in approximately equimolar amounts. The reaction is complete in 2–4 hours. The intermediate product(s) are then isolated:

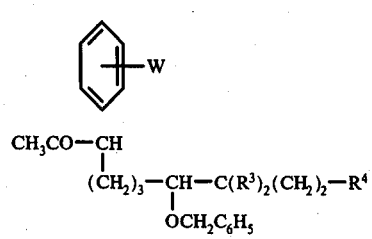
       VIII

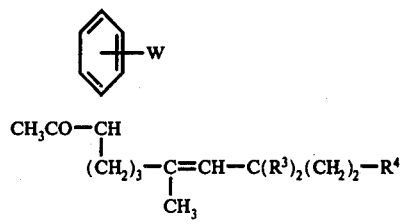
       IX wherein W, $R^3$, and $R^4$ are as defined.

Either of these compounds VIII or IX are then treated with an equimolar amount of base, as NaH, $NaOC_2H_5$, $NaNH_2$, and then alkylated with the reagent:

       X wherein X is halogen, preferably bromine or chlorine, A is as defined in Formula I, and $R^8$ is lower alkyl having 1–5 carbon atoms, preferably ethyl. This reaction is conducted in a similar manner as before, i.e., the reagents are employed in approximately equimolar amounts; the solvent employed is inert, such as DMF, DMF in benzene (1:1) or diglyme. Temperature can be between about 60° C. to 120° C. The reaction is complete within 12–72 hours.

The products isolated are the following:

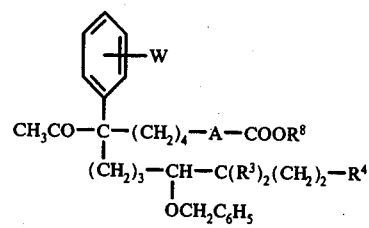
       XI

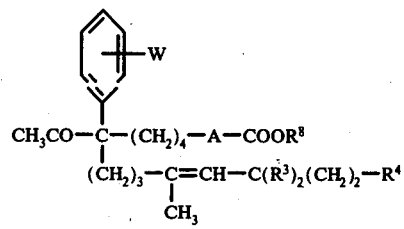
       XII

These are further treated to yield the final product of Formula I.

For example, compound XI is hydrogenated to remove the protecting)-benzyl group and then subjected to mild basic hydrolysis to hydrolyze the ester function and remove $R^8$.

Compound XII is hydrated using a oxymercuration-demercuration process in which the compound is treated with mercuric acetate in aqueous tetrahydrofuran for a prolonged period to effect oxymercuration followed by treatment of the reaction mixture with sodium borohydride to effect demercuration. This product is:

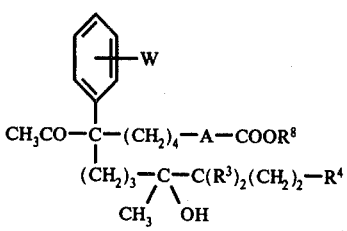

XIII

Mild basic hydrolysis (NaOH is aqueous methanol or ethanol) of the ester function of compound XIII yields the compounds of Formula I.

It should be pointed out that the exact order of reacting either of compounds V or VI with VII, then with X, is not critical, either V or VI or X can be the first reactant. Subsequently, the other of the reactants is reacted with the recovered intermediate. The order described is our preferred route, however.

It can be advantageous from a therapeutic standpoint to prepare compounds of Formula I in which the various asymmetric carbons are exclusively in a certain configuration. For instance, the asymmetric carbon bearing the $R^1$ and $OR^2$ group, in the natural prostaglandins, is in the S configuration; inversion of this center usually produces a reduction in biological activity, although sometimes a marked increase in biological specificity results. Compounds exclusively R and S can be prepared in these processes by using starting materials or intermediates which are optically active, i.e., resolved into their R and S isomeric forms.

These products as prepared in these processes can be derivatized in a variety of ways to yield other products of Formula I.

1. The fundamental processes yield compounds where R is carboxy. To obtain carboxy salts the acid products are dissolved in a solvent such as ethanol, methanol, glyme and the like and the solution treated with an appropriate alkali or alkaline earth hydroxide or alkoxide to yield the metal salt, or with an equivalent quantity of ammonia, amine or quaternary ammonium hydroxide to yield the amine salt. In each instance, the salt either separates from the solution and may be separated by filtration or, when the salt is soluble it may be recovered by evaporation of the solvent. Aqueous solutions of the carboxylic acid salts can be prepared by treating an aqueous suspension of the carboxylic acid with an equivalent amount of an alkaline earth hydroxide or oxide, alkali metal hydroxide, carbonate or bicarbonate, ammonia, an amine, or a quaternary ammonium hydroxide.

To obtain carboxy esters (i.e., compounds where R is alkoxycarbonyl) the acid products are treated in ether with an ethereal solution of the appropriate diazoalkane. For example, methyl esters are produced by reaction of the acid products with diazomethane. To obtain products where R is carbamoyl, substituted carbamoyl or carbazolyl the acid product is first converted to an active Woodward ester. For example, the acid product can be made to react with N-tert-butyl-5-methylisoxazolium perchlorate in acetonitrile in the presence of a base such as triethylamine to yield an active ester in which R is

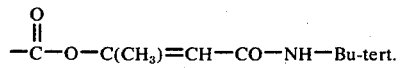

Active esters of this type can be reacted with ammonia to yield products of Formula I where R is carbamoyl, with primary or secondary amines or di-lower-alkylaminoalkylamines to yield products where R is substituted carbamoyl, i.e., $-CONR^6R^7$, and with hydrazine to yield products where R is carbazolyl.

2. The fundamental processes yield products where $R^2$ is hydrogen. In compounds containing no additional hydroxy group and in which $R^1$ is hydrogen, reaction with formic acid, acetic anhydride, propionic anhydride, butyric anhydride, isobutyric anhydride, valeric anhydride, pivalic anhydride and the like, without solvent and at temperatures from 25° to 60° C., gives compounds wherein $R^2$ is formyl, acetyl, propionyl, butyryl, isobutyryl, valeryl, and pivaloyl, respectively.

Methods for obtaining optical antipodes of the compounds of this invention have been described supra, whereby one of the components of the molecule is preresolved prior to its assembly into the whole molecule. Other methods also can be employed; for example, mixtures of racemates may be separated by taking advantage of the physiochemical differences between the components using chromatography and/or fractional crystallization. The racemic products and intermediates of this invention can be resolved into their optically active components by any one of a number of methods of resolution which are well described in the chemical literature.

Those compounds which are carboxylic acids can be converted to the diastereoisomeric salts by treatment with an optically active base such as + or − α-methylbenzylamine, + or − α-(1-naphthyl)-ethylamine, bromine, cinchonine, cinchonidine, or quinine. These diastereoisomeric salts can be separated by fractional crystallization.

The carboxylic acids of this invention also can be converted to esters using an optically active alcohol, such as, estradiol-3-acetate, or d- or l-methanol and the diastereoisomeric esters resolved by crystallization or by chromatographic separation.

Racemic carboxylic acids also may be resolved by reverse phase and absorption chromatography using an optically active support and absorbent.

Compounds of this invention which contain free hydroxyl groups can be esterified with acid chlorides or anhydrides derived from optically active acids, such as, (=)-10-camphorsulfonic acid, (=)-α-bromocamphorsulfonic acid, or d- or 1-6,6'-dinitrodiphenic acid to form esters which can be resolved by crystallization.

Another method of obtaining pure optical isomers involves incubation of the racemic mixture with certain microorganisms such as fungi, by processes well established in the art, and recovering the product formed by the enzymatic transformation.

The methods describes supra are especially effective if one applies the process to a compound where one asymmetric center has been preresolved by the techniques already described The preparation of the intermediates V, VI and X is described in co-pending U.S Ser. No. 302,365, filed Oct. 30, 1972 in the names of Cragoe, Bicking and Smith and in a continuation-in-part application, U.S. Ser. No. 389,901, filed Aug. 23, 1973, both now abandoned.

The intermediates VII are prepared by a process which has been described in the chemical literature (R. V. Heinzelman, "Organic Syntheses" Coll. Vol. IV, John Wiley & Sons, Inc., New York, New York, p. 573) and which may be outlined as follows and wherein W is as described previously:

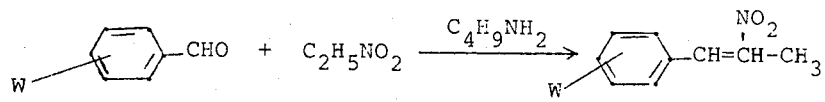

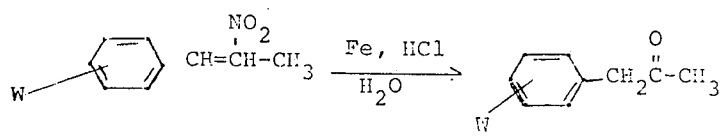

VII

EXAMPLE 1

Preparation of 8-Acetyl-8-chloro-12-hydroxyheptadecanoic Acid

Step A: Preparation of Ethyl 8-Tert.-butoxycarbonyl-9-oxodecanoate

A suspension of 57% sodium hydride in mineral oil (37.05 g. net wt.; 0.88 mole) in a solvent mixture of benzene (400 ml.) and dimethylformamide (400 ml.) is treated, dropwise, over 30 minutes with tert.-butyl acetoacetate (126.56 g.; 0.80 mole). Stirring is continued for an additional 30 minutes. Then ethyl 7-bromoheptanoate (208.50 g.; 0.88 mole) is added, dropwise, over 30 minutes and the mixture is heated at 100° C. for 2½ hours.

The cooled reaction mixture is treated with water (1600 ml.) and the organic layer is separated. The aqueous layer is extracted with ether. The combined organic solutions are washed with saturated sodium chloride solution and then dried over anhydrous sodium sulfate. The solvents are removed under vacuum and the residual oil is distilled to give 158.6 g. (63%) of 8-tert.-butoxycarbonyl-9-oxodecanoate as a yellow oil, b.p. 175°–177°/0.5 mm.

Step B: Preparation of 1-Chloro-4-nonanone

To the Grignard reagent prepared from a mixture of amyl bromide (226.59 g.; 1.5 moles) and magnesium (36.48 g.; 1.5 moles) in ether (1000 ml.) is added, dropwise, during one hour, 4-chlorobutyronitrile (155.34 g.; 1.5 moles). Stirring is continued for an additional one hour. The reaction mixture is poured into a mixture of finely crushed ice (1000 g.) and concentrated hydrochloric acid (750 ml.). The ether layer is separated quickly and discarded. The aqueous layer is heated on a steam bath for one hour to hydrolyze the intermediate imine and cause the separation of the ketone as an oil. After cooling, the oil is extracted with ether and the combined extracts are washed with saturated sodium chloride solution and dried over anhydrous sodium sulfate. The solvent is removed under vacuum and the residual oil is distilled to give 69.0 g. (26%), of 1-chloro-4-nonanone as a colorless oil, b.p. 115°–117°/14 mm.; pmr (CDCl$_3$)$\delta$0.90 (3H,t), 3.56 (2H,t,CH$_2$Cl).

Step B(2): Preparation of 1-Chloro-4-nonanol

A suspension of sodium borohydride (6.62 g.; 0.175 mole) and sodium hydroxide (1.3 g.) in ethanol (310 ml.) is treated, dropwise, over 1 hour with 1-chloro-4-nonanone (61.40 g.; 0.349 mole) while the temperature is maintained at 45°–50°. Stirring is continued for one hour, longer without external cooling.

The reaction mixture is acidified with concentrated hydrochloric acid to the Cargo red endpoint and then the ethanol is removed under reduced pressure. The residue is treated with water (200 ml.) and the resulting oil is extracted with ether. The combined extracts are washed with saturated sodium chloride solution and dried over anhydrous sodium sulfate. The solvent is removed under vacuum to give 1-chloro-4-nonanol as a light yellow residual oil, yield 58.85 g.; ir (neat) 3400 cm$^{-1}$.

Step B(3): Preparation of 1-Chloro-4-acetoxynonane

A mixture of 1-chloro-4-nonanol (111.99 g.; 0.627 mole) and acetic anhydride (128.0 g.; 1.254 moles) is heated on a steam bath for 1½ hours.

The volatile materials are removed under reduced pressure and the residual oil is distilled to give 88.6 g. (64%) of 1-chloro-4-acetoxynonane as a colorless oil, b.p. 130°–133°/14 mm.; pmr (CDCl$_3$)$\delta$0.89 (3H,t), 2.02 (3H, s CH$_3$COO), 3.53 (2H,t CH$_2$Cl), 4.89 (1H,m). Anal. Calcd. for C$_{11}$H$_{21}$ClO$_2$: C, 59.85; H, 9.59. Found: C, 59.87; H, 9.67.

Step B(4): Preparation of Ethyl 8-Acetyl-8-tert.-butoxycarbonyl-12-acetoxyheptadecanoate A suspension of 57% sodium hydride in mineral oil (3.03 g. net wet., 0.072 mole) in a solvent mixture of benzene (40 ml.) and dimethylformamide (40 ml.) is treated, dropwise, over a period of 30 minutes with ethyl 8-tert.-butoxycarbonyl-9-oxodecanoate (20.41 g., 0.065 mole). Stirring is continued for an additional period of 30 minutes. Then 1-chloro-4-acetoxynonane (15.80 g., 0.072 mole) is added, dropwise, over 30 min. Potassium iodide (50 mg.) is added and the mixture heated at 100° for 66 hours.

The reaction mixture is cooled, treated with water (160 ml.) and the organic layer separated. The aqueous layer is extracted with ether. The combined organic extracts are washed with a saturated aqueous sodium chloride solution and then dried over anhydrous sodium sulfate. The solvents are removed by evaporation in vacuo to give a residual oil of ethyl 8-acetyl-8-tert.-butoxycarbonyl-12-acetoxyheptadecanoate. The yield is 32.04 g.; pmr (CDCl$_3$)$\delta$0.90 (3H,t), 1.45 (9H,s), 2.02 (3H,s CH$_3$COO), 2.12 (3H,s CH$_3$CO), 4.13 (2H,q).

Step C: Preparation of Ethyl 8-Acetyl-12-acetoxyheptadecanoate

A mixture of ethyl 8-acetyl-8-tert.-butoxycarbonyl-12-acetoxyheptadecanoate (32.04 g.; 0.0643 mole), p-toluenesulfonic acid monohydrate (1.10 g.) and toluene (110 ml.) is heated under reflux for 18–22 hours. The CO$_2$ evolved is indicated by bubbling the gas into aqueous Ba(OH)$_2$.

The cooled reaction mixture is washed with saturated sodium bicarbonate solution (25 ml.), saturated sodium chloride solution (2 × 25 ml.) and then dried over anhydrous sodium sulfate. The solvent is removed under vacuum to give 26.69 g. (theory 25.63 g.) of a residual oil. The oil is purified by column chromatography on silica gel with chloroform as an eluant. There is obtained 9.6 g. (38%) of ethyl 8-acetyl-12-acetoxyheptadecanoate, pmr (CDCl$_3$)δ0.90 (3H,t), 2.02 (3H,s CH$_3$COO), 2.12 (3H,s CH$_3$CO), 4.13 (2H,q), 4.84 (1H, m HCOCOCH$_3$).

Anal. Calcd. for C$_{23}$H$_{42}$O$_5$: C, 69.31; H, 10.62. Found: C, 69.47; H, 10.83.

Step D: Preparation of 8-Acetyl-12-hydroxyheptadecanoic Acid

Ethyl 8-acetyl-12-acetoxyheptadecanoate (12.21 g., 0.0306 mole) is added to a solution of sodium hydroxide (3.67 g., 0.0918 mole) in water (17 ml.) and methanol (153 ml.). The resulting solution is allowed to stand for 72 hours at 25° C. Most of the methanol is removed by evaporation in vacuo. The residual solution is diluted with water (150 ml.) and extracted with ether. The aqueous layer is acidified to Congo red paper with acid. The ether extract is washed with water.

The ether extract is dried over anhydrous sodium sulfate and evaporated in vacuo to produce 9.65 g. (95%) of 8-acetyl-12-hydroxyheptadecanoic acid as a viscous yellow liquid. This material is purified by column chromatography on silica gel with 2% methanol in chloroform as the eluant. There is obtained 6.9 g. (69%) of pure 8-acetyl-12-hydroxyheptadecanoic acid as a colorless liquid, pmr (CDCl$_3$) δ0.88 (3H,t), 2.12 (3H, S CH$_3$CO), 3.64 (1H, m HCOH), 6.65 (2H, s OH and COOH).

Anal. Calcd. for C$_{19}$H$_{36}$O$_4$: C, 69.47; H, 11.05. Found: C, 69.55; H, 11.22.

Step E: Preparation of 8-Acetyl-8-chloro-12-hydroxyheptadecanoic Acid

A mixture of 8-acetyl-12-hydroxyheptadecanoic acid (16.4 g., 0.05 mole), cupric chloride dihydrate (20.5 g., 0.12 mole), lithium chloride (2.5 g., 0.06 mole) and dimethylformamide (30 ml.) is heated with stirring for 16 hours on the steam bath. The reaction mixture is then cooled and treated with water. The oil which separates is taken up in ether, washed with water and brine and dried over sodium sulfate. The ether is distilled to leave the product as an orange oil, weight 19.3 g. The product is purified by chromatography on silica gel with 2% methanol in chloroform as eluant. There is obtained 3.5 g. (19%) of 8-acetyl-8-chloro-12-hydroxyheptadecanoic acid as a light yellow oil; pmr (CDCl$_3$) δ0.88 (3H,t), 2.34 (3H,s CH$_3$CO), 3.65 (1H,m HCOH).

Anal. Calcd. for C$_{19}$H$_{35}$ClO$_4$: C, 62.88; H, 9.72. Found: C, 62.48; H, 9.65.

By following exactly the same procedure but employing 8-acetyl-12(R)-hydroxyheptadecanoic acid, there is obtained 8-acetyl-8-chloro-12(R)-hydroxyheptadecanoic acid.

Similarly, by following exactly the same procedure but employing 8-acetyl-12(S)-hydroxyheptadecanoic acid, there is obtained 8-acetyl-8-chloro-12(S)-hydroxyheptadecanoic acid.

EXAMPLE 2

Preparation of 8-Acetyl-8-bromo-12-hydroxyheptadecanoic Acid

By following the procedure of Example 1, Step E, but substituting cupric bromide and lithium bromide for cupric chloride dihydrate and lithium chloride, there is obtained 8-acetyl-8-bromo-12-hydroxyheptadecanoic acid as a viscous yellow oil purified by chromatography an silica gel with 2% methanol in chloroform as the eluant.

EXAMPLE 3

Preparation of 8-Acetyl-12-hydroxy-8-phenylheptadecanoic Acid

Step A: 1-Chloro-4-chloromethoxynonane

A gentle stream of dry HCl gas is passed into a suspension of the crude 1-chloro-4-nonanol (40.66 g., 0.23 mole) and S-trioxane (6.90 g., 0.077 mole) for 14 hours. The resulting two-phase mixture is dried over CaCl$_2$. The CaCl$_2$ is removed by filtration and the filtrate is fractionally distilled to obtain 1-chloro-4-chloromethoxynonane (19.05 g., 0.084 mole, 31% yield, b.p. 140°–143°/14 mm.).

Step B: Preparation of 1-Chloro-4-benzyloxynonane

A solution of bromobenzene (13.18 g., 0.084 mole) in ether (50 ml.) is added to a suspension of Mg (2.04 g., 0.084 mole) in ether (50 ml.) dropwise so as to maintain a gentle reflux. After complete addition of the bromobenzene, the mixture is heated on a steam bath for an additional hour. The reaction mixture is then cooled to 5°–10° C. by means of an ice-water bath, and 1-chloro-4-chloromethoxynonane (19.05 g., 0.084 mole) is added dropwise over 15 minutes. The resulting suspension is stirred for 18 hours at room temperature. The reaction mixture is diluted with ether (100 ml.), cooled to 0°–5° C., and cold water (75 ml.) is added with vigorous stirring while the temperature is kept below 5° C. Let stir a 0°–5° C. for about 15 minutes. The aqueous phase is separated from the ether phase (A), and the aqueous layer is extracted with ether (150 ml., B). Organic solution A is combined with B, washed with H$_2$O (100 ml.), 5% K$_2$CO$_3$ (100 ml.), again with H$_2$O (100 ml.), finally with saturated NaCl solution, and is dried over anhydrous Na$_2$SO$_4$. Removal of the solvent in vacuo yields 1-chloro-4-benzyloxynonane (19.28 g., 0.072 mole, 85.7% yield).

Step C: Preparation of 3-Phenyl-7-benzyloxy-2-dodecanone

Sodium hydride (1.7 g., 0.071 mole) is suspended in a mixture of benzene (50 ml.) and dimethylformamide (50 ml.) and phenylacetone (8.7 g., 0.071 mole) is added dropwise. The resulting mixture is heated on the steam bath for one hour and then cooled to room temperature. 1-Chloro-4-benzyloxynonane (18.2 g., 0.071 mole) is added dropwise and the mixture then heated and stirred on the steam bath for 24 hours. The mixture is cooled, poured into water (300 ml.) and the oily product taken up in ether and dried over sodium sulfate. The solvent is removed in vacuo and the residual oil is fractionally distilled to yield 12.2 g. (46%) of 3-phenyl-7-benzyloxy-2-dodecanone, b.p. 184°–190°/0.1 mm Hg.

Step D: Preparation of Ethyl 8-Acetyl-8-phenyl-12-benzyloxyheptadecanoate

Sodium hydride (0.8 g., 0.033 mole) is suspended in a mixture of benzene (50 ml.) and dimethylformamide (50 ml.) and 3-phenyl-7-benzyloxy-2-dodecanone (12.1 g., 0.033 mole) is added dropwise. The resulting mixture is heated on the steam bath for one hour and then cooled to room temperature. Ethyl 7-bromoheptanoate (8.8 g., 0.037 mole) is added dropwise and the mixture is heated on the steam bath for 24 hours. The reaction mixture is cooled, poured into water (200 ml.) and the oily product taken up into ether and dried over sodium sulfate. The solvent is distilled in vacuo to leave 14 g. of ethyl 8-acetyl-8-phenyl-12-benzyloxyheptadecanoate as a yellow oil which is used in Step G without further purification.

Step E: Preparation of 8-Acetyl-8-phenyl-12-benzyloxyheptadecanoic Acid

A mixture of ethyl 8-acetyl-8-phenyl-12-benzyloxyheptadecanoate (14 g., crude), sodium hydroxide (2.0 g., 0.05 mole) and methanol (150 ml.) is stirred for 48 hours. The methanol is removed in vacuo; and the residual oil is poured into H$_2$O (100 ml.), acidified with 6 N HCl (100 ml.), extracted with ether, and the combined ether extracts dried over anhydrous Na$_2$SO$_4$. The ether is removed in vacuo, and the residual oil is chromatographed through a silica gel column (95% CHCH$_3$-5% MeOH) to obtain 8-acetyl-8-phenyl-12-benzyloxyheptadecanoic acid (1.43 g., slightly impure).

Step F: Preparation of 8-Acetyl-8-phenyl-12-hydroxyheptadecanoic Acid

8-Acetyl-8-phenyl-12-benzyloxyheptadecanoic acid (1.42 g., slightly impure) is dissolved in EtOH (50 ml.), and is hydrogenated over 10% palladium on carbon at atmospheric pressure and 25° C. The hydrogenation is stopped after 2 hours, the catalyst is filtered off, and the solvent is removed in vacuo to obtain the product as a crude viscous yellowish oil. This oil is chromatographed through a silica gel column (CHCl$_3$) to obtain 8-acetyl-8-phenyl-12-hydroxyheptadecanoic acid as a virtually colorless oil (350 mg.).

Anal. Calcd. for C$_{25}$H$_{40}$O$_4$: C, 74.21; H, 9.97. Found: C, 74.38; H, 9.80.

EXAMPLE 4

8-Acetyl-8-methyl-12-hydroxyheptadecanoic Acid

Step A: Preparation of Ethyl 8-Acetyl-8-bromo-12-acetoxyheptadecanoate

Bromine (16.7 g., 0.104 mole) dissolved in carbon tetrachloride (100 ml.) is added dropwise to a stirred solution of ethyl 8-acetyl-12-acetoxyheptadecanoate (Example 1, Step C) (37.4 g., 0.094 mole) in carbon tetrachloride (200 ml.) during one hour. The solvent is distilled in vacuo. The residual oil is dissolved in ether and washed with dilute sodium bicarbonate, water and brine and dried over sodium sulfate. Evaporation of the ether leaves the crude bromo ester as a yellow oil weighing 43 g. It is purified by column chromatography on silica gel with benzene as the eluant. This procedure serves to separate the desired bromo ester from a small amount of a by-product, ethyl 8-bromoacetyl-8-bromo-12-acetoxyheptadecanoate. Ethyl 8-acetyl-8-bromo-12-acetoxyheptadecanoate is thus obtained as a pale yellow oil weighing 12.7 g. (28%).

Ethyl 8-Acetyl-8-methyl-12-acetoxy heptadecanoate

Step B: Cupruous iodide (7.1 g., 0.037 mole) is suspended in ether (150 ml.) and a 1.66 M solution of methyl lithium in ether (45 ml., 0.075 mole) is added dropwise during 30 minutes. Ethyl 8-acetyl-8-bromo-12-acetoxyheptadecanoate (11.9 g., 0.025 mole) is added dropwise during 30 minutes. The temperature is kept at −4° C to −2° C. during these operations by means of a salt bath. Stirring is continued at this temperature for another 30 minutes; then the mixture is stirred for 2 hours without cooling. The reaction mixture is then treated with 200 ml. of saturated ammonium chloride solution. The organic layer is separated, washed with brine and dried over sodium sulfate. Distillation of the solvent in vacuo leaves the crude product as an orange oil weighing 9.2 g. The product is purified by column chromatography using 250 g. of silica gel and chloroform as the eluant. Ethyl 8-acetyl-8-methyl-12-acetoxyheptadecanoate is obtained as yellow viscous oil.

Step C: Preparation of 8-Acetyl-8-methyl-12-hydroxyheptadecanoic Acid

By following the hydrolytic procedure described in Example 1, Step D, but substituting an equimolar amount of ethyl 8-acetyl-8-methyl-12-acetoxyheptadecanoate for the ethyl 8-acetyl-12-acetoxyheptadecanoate of the example, there is obtained 8-acetyl-8-methyl-12-hydroxyheptadecanoic acid as a colorless viscous oil.

In a like manner, the following compounds can be prepared:

EXAMPLE 5

Preparation of 8-Acetyl-8-chloro-12-hydroxy-16-methylheptadecanoic Acid

By following the procedure described in Example 1, Step E, but substituting 8-acetyl-12-hydroxy-16-methylheptadecanoic acid for the 8-acetyl-12-hydroxyheptadecanoic acid therein employed, there is obtained 8-acetyl-8-chloro-12-hydroxy-16-methylheptadecanoic acid.

EXAMPLE 6

Preparation of 8-Acetyl-8-chloro-12-hydroxy-16,16-dimethylheptadecanoic Acid

By following the procedure described in Example 1, Step E, but substituting 8-acetyl-12-hydroxy-16,16-dimethylheptadecanoic acid for the 8-acetyl-12-hydroxyheptadecanoic acid therein employed, there is obtained 8-acetyl-8-chloro-12-hydroxy-16,16-dimethylheptadecanoic acid.

EXAMPLE 7

Preparation of 8-Acetyl-8-chloro-12-hydroxy-17,17,17-trifluoroheptadecanoic Acid By following the procedure described in Example 1, Step E, but substituting 8-acetyl-12-hydroxy-17,17,17-trifluoroheptadecanoic acid for the 8-acetyl-12-hydroxyheptadecanoic acid therein employed, there is obtained 8-acetyl-8-chloro-12-hydroxy-17,17,17-trifluoroheptadecanoic acid.

EXAMPLE 8

Preparation of 8-acetyl-8-chloro-12-methyl-12-hydroxyheptadecanoic Acid

By following the procedure described in Example 1, Step E, but substituting 8-acetyl-12-methyl-12-hydroxyheptadecanoic acid for the 8-acetyl-12-hydroxyheptadecanoic acid therein employed, there is obtained 8-acetyl-8-chloro-12-methyl-12-hydroxyheptadecanoic acid.

EXAMPLE 9

Preparation of
8-Acetyl-8-chloro-12-hydroxy-13,13-dimethylheptadecanoic Acid

By following the procedure described in Example 1, Step E, but substituting 8-acetyl-12-hydroxy-13,13-dimethylheptadecanoic acid for the 8-acetyl-12-hydroxy-heptadecanoic acid therein employed, there is obtained 8-acetyl-8-chloro-12-hydroxy-13,13-dimethylheptadecanoic acid.

EXAMPLE 10

Preparation of
(5-Acetyl-5-chloro-9-hydroxytetradecyloxy)-acetic Acid

By following the procedure described in Example 1, Step E, but substituting (5-acetyl-9-hydroxytetradecyloxy)acetic acid for the 8-acetyl-12-hydroxyheptadecanoic acid therein employed, there is obtained (5-acetyl-5-chloro-9-hydroxytetradecyloxy)acetic acid.

EXAMPLE 11

Preparation of
8-Acetyl-8-chloro-11-(1-hydroxycyclohexyl)-undecanoic Acid

By following the procedure described in Example 1, Step E, but substituting 8-acetyl-11-(1-hydroxycyclohexyl)undecanoic acid for the 8-acetyl-12-hydroxyheptadecanoic acid therein employed, there is obtained 8-acetyl-8-chloro-11-(1-hydroxycyclohexyl)undecanoic acid.

EXAMPLE 12

Preparation of
2-Methyl-8-acetyl-8-bromo-12-hydroxyheptadecanoic Acid

By following essentially the procedure of Example 2 but substituting 2-methyl-8-acetyl-12-hydroxyheptadecanoic acid for the 8-acetyl-12-hydroxyheptadecanoic acid therein employed, there is obtained 2-methyl-8-acetyl-8-bromo-12-hydroxyheptadecanoic acid.

EXAMPLE 13

Preparation of
3-Methyl-8-acetyl-8-bromo-12-hydroxyheptadecanoic Acid

By following essentially the procedure of Example 2, but substituting 3-methyl-8-acetyl-12-hydroxyheptadecanoic acid for the 8-acetyl-12-hydroxyheptadecanoic acid therein employed, there is obtained 3-methyl-8-acetyl-8-bromo-12-hydroxyheptadecanoic acid.

EXAMPLE 14

Preparation of
2,2-Dimethyl-8-acetyl-8-bromo-12-hydroxyheptadecanoic Acid

By following essentially the procedure of Example 2, but substituting 2,2-dimethyl-8-acetyl-12-hydroxyheptadecanoic acid for the 8-acetyl-12-hydroxyheptadecanoic acid therein employed, there is obtained 2,2-dimethyl-8-acetyl-8-bromo-12-hydroxyheptadecanoic acid.

EXAMPLE 15

Preparation of
3,3-Dimethyl-8-acetyl-8-chloro-12-hydroxyheptadecanoic Acid

By following essentially the procedure of Example 1, Step E, but substituting 3,3-dimethyl-8-acetyl-12-hydroxyheptadecanoic acid for the 8-acetyl-12-hydroxyheptadecanoic acid therein employed, there is obtained 3,3-dimethyl-8-acetyl-8-chloro-12-hydroxyheptadecanoic acid.

EXAMPLE 16

Preparation of
8-Acetyl-8-(4-fluorophenyl)-12-hydroxyheptadecanoic Acid

By following the procedure described in Example 3, but substituting (4-fluorophenyl)acetone for the phenylacetone employed in Step C, there are obtained successively from that point: 3-(4-fluorophenyl)-7-benzyloxy-2-dodecanone (Step C); ethyl 8-acetyl-8-(4-fluorophenyl)-12-benzyloxy-heptadecanoate (Step D); 8-acetyl-8-(4-fluorophenyl)-12-benzyloxyheptadecanoic acid (Step E); and 8-acetyl-8-(4-fluorophenyl)-12-hydroxyheptadecanoic acid (Step F).

EXAMPLE 17

Preparation of
8-Acetyl-8-(2-methylphenyl)-12-hydroxyheptadecanoic Acid

By following the procedures described in Example 3, but substituting (2-methylphenyl)acetone for the phenylacetone employed in Step C, there are obtained successively from that point: 3-(2-methylphenyl)-7-benzyloxy-2-dodecanone (Step C); ethyl 8-acetyl-8-(2-methylphenyl)-12-benzyloxyheptadecanoate (Step D); 8-acetyl-8-(2-methylphenyl)-12-benzyloxyheptadecanoic acid (Step E); and 8-acetyl-(2-methylphenyl)-12-hydroxyheptadecanoic acid (Step F).

EXAMPLE 18

Preparation of
8-Acetyl-8-(3,4-dichlorophenyl)-12-hydroxyheptadecanoic Acid

By following the procedures described in Example 3, but substituting (3,4-dichlorophenyl)acetone for the phenylacetone employed in Step C, there are obtained successively from that point: 3-(3,4-dichlorophenyl)-7-benzyloxy-2-dodecanone (Step C); ethyl 8-acetyl-8-(3,4-dichlorophenyl)-12-benzyloxyheptadecanoic acid (Step E); and 8-acetyl-8-(3,4-dichlorophenyl)-12-hydroxyheptadecanoic acid (Step F).

EXAMPLE 19

Preparation of
8-Acetyl-8-(4-methoxyphenyl)-12-hydroxyheptadecanoic Acid

By following the procedures described in Example 3, but substituting (4-methoxyphenyl)acetone for the phenylacetone employed in Step C, there are obtained successively from that point: 3-(4-methoxyphenyl)-7-benzyloxy-2-dodecanone (Step C); ethyl 8-acetyl-8-(4-methoxyphenyl)-12-benzyloxy-heptadecanoate (Step D); 8-acetyl-8-(4-methoxyphenyl)-12-benzyloxyheptadecanoic acid (Step E); and 8-acetyl-8-(4-methoxyphenyl)-12-hydroxyheptadecanoic acid (Step F).

EXAMPLE 20

Preparation of
8-Acetyl-8-phenyl-12-hydroxynonadecanoic Acid

By following the procedures described in Example 3, but substituting in Step A 1-chloro-4-undecanol for the 1-chloro-4-nonanol therein employed there are obtained successively: 1-chloro-4-chloromethoxyundecane (Step A); 1-chloro-4-benzyloxyundecane (Step B); 3-phenyl-7-benzyloxy-2-tetradecanone (Step C); ethyl 8-acetyl-8-phenyl-12-benzyloxynonadecanoate (Step D); 8-acetyl-8-phenyl-12-benzyloxynonadecanoic acid (Step E); and 8-acetyl-8-phenyl-12-hydroxynonadecanoic acid (Step F).

EXAMPLE 21

Preparation of
8-Acetyl-8-phenyl-12-hydroxy-12-methylheptadecanoic Acid

Step A: Preparation of 3-Phenyl-7-methyl-6-dodecen-2-one

By following the procedure of Example 3, Step C, but substituting 1-chloro-4-methyl-3-nonene for the 1-chloro-4-benzyloxynonane therein employed, there is obtained 3-phenyl-7-methyl-6-dodecen-2-one.

Step B: Preparation of Ethyl 8-Acetyl-8-phenyl-12-methyl-11-heptadecenoate

By following the procedure of Example 3, Step D, but substituting 3-phenyl-7-methyl-6-dodecen-2-one for the 3-phenyl-7-benzyloxy-2-dodecanone therein employed, there is obtained ethyl 8-acetyl-8-phenyl-12-methyl-11-heptadecenoate.

Step C: Preparation of 8-Acetyl-8-phenyl-12-methyl-11-heptadecenoic Acid

By following the hydrolytic procedure of Example 3, Step E, but substituting ethyl 8-acetyl-8-phenyl-12-methyl-11-heptadecenoate for the ethyl 8-acetyl-8-phenyl-12-benzyloxyheptadecanoate therein employed, there is obtained 8-acetyl-8-phenyl-12-methyl-11-heptadecenoic acid.

Step D: 8-Acetyl-8-phenyl-12-hydroxy-12-methyl-heptadecanoic Acid

Mercuric acetate (3.8 g., 0.012 mole) is dissolved in water (12 ml.) and tetrahydrofuran (20 ml.) is added to give a suspension of a yellow solid. Then, 8-acetyl-8-phenyl-12-methyl-11-heptadecanoic acid (4.8 g., 0.012 mole) in tetrahydrofuran (20 ml.) is added, and the mixture stirred at room temperature for 24 hours. After 6 hours, the yellow suspended solid has disappeared and a cloudy solution results. To the solution is added 3M sodium hydroxide solution (12 ml.), followed by 0.5M sodium borohydride solution in 3M solution hydroxide (12 ml.). Liquids are decanted from the precipitated mercury. The organic layer is taken up in ether, washed with three portions of water and dried over sodium sulfate. Evaporation of the ether leaves 8-acetyl-8-phenyl-12-hydroxy-12-methyl-heptadecanoic acid as a yellow viscous oil which is purified by chromatography on silica gel with 4% methanol in chloroform as eluant.

EXAMPLE 22

Preparation of
8-Acetyl-8-chloro-12-acetoxyheptadecanoic Acid

A mixture of 8-acetyl-8-chloro-12-hydroxyheptacecanoic acid (0.1 g., 0.025 mole) and acetic anhydride (6.1 g., 0.06 mole) is heated at 60° C. for 18 hours. The mixture is then cooled and dissolved in 80 ml. ethyl ether. The solution is extracted with an ice-cold solution of 8 g. sodium hydroxide in 150 ml. water. The basic solution is separated and acidified with concentrated hydrochloric acid. The oily acid which separates is taken up in ether, washed with water and dried over sodium sulfate. The ether is evaporated to leave 9.0 g. of the oily crude product.

The product is purified by chromatography on a column containing 150 g. of silica gel and with 1% methanol in chloroform as the eluting solvent. There is obtained 8-acetyl-8-chloro-12-acetoxyheptadecanoic acid, a colorless viscous oil.

EXAMPLE 23

Preparation of Methyl
8-Acetyl-8-chloro-12-hydroxyheptadecanoate

A solution of diazomethane (approx. 2.5 g., 0.06 mole) in ether (100 ml.) is mixed with a solution of 8-acetyl-8-chloro-12-hydroxyheptadecanoic acid (10.9 g., 0.03 mole) in ether (50 ml.). The resulting solution is allowed to stand 4 hours at room temperature. Acetic acid is then added to destroy the excess diazomethane and the solution is washed with dilute sodium bicarbonate solution and water and dried over sodium sulfate. Evaporation of volatile materials at reduced pressure yields methyl 8-acetyl-8-chloro-12-hydroxyheptadecanoate, a colorless viscous oil.

EXAMPLE 24

Preparation of
N-[2-(Dimethylamino)ethyl]-8-acetyl-8-phenyl-12-hydroxyheptadecanamide A solution of 8-acetyl-8-phenyl-12-hydroxyheptadecanoic acid (4.04 g., 10 millimole), Example 1, Step D, triethylamine (1.74 ml., 12.5 millimole) and distilled water (18 ml., 1.0 mole) in acetonitrile (100 ml.) is treated with N-t-butyl-5-methylisoxazolium perchlorate (3.0 g., 12.5 millimole). The resulting solution is evaporated in vacuo (water aspirator) at 20°–23° C. for 4 hours providing a tacky residue which is triturated with water (150 ml.) at 0°–5° C. for 15 minutes. After decanting the aqueous phase, the oily residue is dissolved in benzene-ether [(1:1), 200 ml.]. The organic extract is dried over sodium sulfate, filtered and evaporated in vacuo at 35°–40° C. providing the desired "active ester", N-t-butyl-3-(8-acetyl-8-phenyl-12-hydroxyheptadecanoyloxy)-crotonamide, as a pale yellow oil.

A solution of 2-dimethylaminoethylamine (0.88 g., 10 millimole) in acetonitrile (25 ml.) is added to a solution of the "active ester" in acetonitrile (25 ml.) providing a clear solution which is stirred at 25° C. for 17 hours. The solvent is removed in vacuo at 40°–50° C. leaving a residual oil which is partitioned between ether (200 ml.) and water (2 × 100 ml.). The organic extract is washed with saturated brine (2 × 100 ml.), dried over sodium sulfate, filtered and evaporated in vacuo at 40°–50° C. providing a tan, crude oil.

The oil is partitioned between 5% hydrochloric acid (100 ml.) and ether (2 × 100 ml.). The aqueous acid phase is slowly basicified with sodium bicarbonate (16.8 g., 0.2 mole), then with 40% aqueous sodium hydroxide (10 ml.) providing a heterogeneous mixture which is extracted with ether (200, 100 ml.). The organic extract is washed with saturated brine (200 ml.), dried over sodium sulfate, filtered and evaporated in vacuo at 40°–50° C. leaving the title compound as a pale yellow oil. (2.8 g., 76%); pmr (CDCl$_3$) δ0.88 (3H,t).

EXAMPLE 25

| Capsule Formulation | |
|---|---|
| 8-Acetyl-8-methyl-12-hydroxyhepta-decanoic Acid | 50 gm. |
| Stearic Acid (U.S.P. triple pressure) | 125 gm. |
| Pluronic F-68 | 7.5 gm. |
| Corn starch | 125 gm. |

The stearic acid and pluronic are united in a vessel and melted using a water bath at 60°–65° C. The heating is discontinued and the 8-acetyl-8-methyl-12-hydroxyheptadecanoic acid is dispersed into the mixture and the corn starch is added with stirring which is continued until the mixture cools to ambient temperature. The mixture is reduced to granules by screening and placed in a number of 0 hard gelatin containing 307.5 mg. of total solids and 50 mg. of the compound per capsule.

EXAMPLE 26

| Parenteral Formulation of a Multidose Solution for Intramuscular and Intravenous Use | |
|---|---|
| 8-Acetyl-8-chloro-12-hydroxyhepta-decanoic Acid | 1 gram |
| Tris(hydroxymethyl)amino-methane (Reagent Grade Tham) | q.s. to adjust solution to pH 7.4 |
| Sodium chloride (U.S.P.) | q.s. to yield isotonic solution |
| Methylparaben | 10 mg. |
| Propylparaben | 1 mg. |
| Distilled water (pyrogen-free) | q.s. to 10 ml. |

The 8-acetyl-8-chloro-12-hydroxyheptadecanoic acid suspended in about 6 ml. of the water is treated with tris(hydroxymethyl)aminomethane with stirring until the pH reaches 7.4. The methylparaben and propylparaben are added with stirring and sufficient sodium chloride added to produce an isotonic solution. After water is added to bring the final volume to 10 ml., the solution is sterilized by membrane filtration and placed in a vial by an aseptic technique. The solution contains the Tham salt of 8-acetyl-8-chloro-12-hydroxyheptadecanoic acid equivalent to 100 mg./ml. of the free acid.

EXAMPLE 27

| Preparation of Suppositories | |
|---|---|
| 8-Acetyl-8-bromo-12-hydroxyhepta-decanoic Acid | 200 gm. |
| Butylated hydroxyanisole | 82 mg. |
| Butylated hydroxytoluene | 82 mg. |
| Ethylenediamine tetraacetic acid | 163 mg. |
| Glycerine, U.S.P. | 128 gm. |
| Sodium chloride, microfine | 52.5 gm. |
| Polyethylene glycol 6000 | 128 gm. |
| Polyethylene glycol 4000 | 1269 gm. |

The polyethylene glycol 4000 and polyethylene glycol 6000 were placed in a vessel surrounded by a water bath at such a temperature required to maintain the melted contents at 60°–65° C. To the melt is added the butylated hydroxyanisole and butylated hydroxytoluene with stirring. Then the ethylenediamine tetraacetic acid and microfine sodium chloride are added to and dispersed in the mixture. The 8-acetyl-8-bromo-12-hydroxyheptadecanoic acid is then added and dispersed into the mixture. Finally, the temperature is lowered to 55°–60° C. and the glycerine added and dispersed.

While maintaining the temperature of 55°–60° C. and continuous mixing, the melt is dispersed into plastic suppository cavities of a conventional suppository cold-molding device. The suppositories thus prepared contain a total of 1.7778 gm. of contents of which 200 mg. are 8-acetyl-8-bromo-12-hydroxyheptadecanoic acid.

What is claimed is:

1. The compound having the following formula:

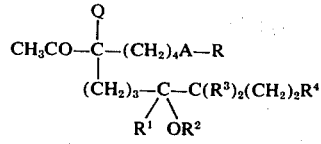

wherein

R is carboxy, a carboxy salt, or a carboxy alkyl ester;
A is ethylene, trimethylene, α-methylethylene, β-methylethylene, α,α-dimethylethylene, or β,β-dimethylethylene;
Q is chloro or bromo; $R^1$ is hydrogen or methyl;
$R^2$ is hydrogen;
$R^3$ is hydrogen or methyl; and
$R^4$ is hydrogen or loweralkyl.

2. The compound of claim 1 which has the formula:

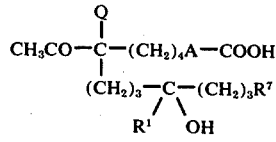

wherein A is ethylene, trimethylene, α-methylethylene, β-methylethylene, α,α-dimethylethylene, or β,β-dimethylethylene; $R^1$ is hydrogen or methyl; $R^7$ is hydrogen or loweralkyl; and Q is chloro or bromo.

3. The compound of claim 2 wherein $R^7$ is loweralkyl having 2–5 carbon atoms.

4. The compound of claim 3 wherein A is ethylene, and $R^7$ is ethyl.

5. 8-Acetyl-8-chloro-12-hydroxyheptadecanoic acid, the compound of claim 4 wherein Q is chloro and $R^1$ is hydrogen.

6. 8-Acetyl-8-chloro-12-(R)-hydroxyheptadecanoic acid, the compound of claim 5 wherein the carbon atom bearing the hydroxy group is in the R configuration.

7. 8-Acetyl-8-chloro-12-(S)-hydroxyheptadecanoic acid, the compound of claim 5 wherein the carbon atom bearing the hydroxy group is in the S configuration.

8. The compound of claim 4 wherein Q is bromo and $R^1$ is hydrogen which is 8-acetyl-8-bromo-12-hydroxyheptadecanoic acid.

9. 8-Acetyl-8-chloro-12-hydroxy-16-methyl-heptadecanoic acid, the compound of claim 3 wherein A is ethylene, Q is chloro, $R^1$ is hydrogen and $R^7$ is isopropyl.

10. 8-Acetyl-8-chloro-12-hydroxy-16,16-dimethyl-heptadecanoic acid, the compound of claim 3 wherein A is ethylene, $R^7$ is tert-butyl, Q is chloro and $R^1$ is hydrogen.

11. The compound of claim 2 which has the formula:

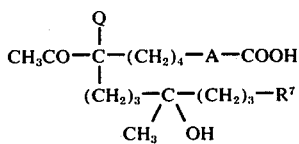

wherein A is ethylene, trimethylene, α-methylene, β-methylethylene, α,α-dimethylethylene, or β,β-dimethylethylene; $R^7$ is hydrogen or loweralkyl of 1–4 carbon atoms; and Q is chloro or bromo.

12. 8-Acetyl-8-chloro-12-hydroxy-12-methylheptadecanoic acid, the compound of claim 11 wherein A is ethylene, $R^7$ is ethyl, and Q is chloro.

13. The compound of claim 2 which has the formula:

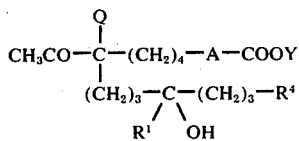

wherein A is ethylene, trimethylene, α-methylethylene, β-methylethylene, α,α-dimethylethylene, or β,β-dimethylethylene; $R^7$ is hydrogen or loweralkyl; and Q is chloro or bromo.

14. 2-Methyl-8-acetyl-8-bromo-12-hydroxyheptadecanoic acid, the compound of claim 13 wherein A is α-methylethylene, $R^7$ is ethyl, and Q is bromo.

15. 3-Methyl-8-acetyl-8-bromo-12-hydroxyheptadecanoic acid, the compound of claim 13 wherein A is β-methylethylene, $R^7$ is ethyl and Q is bromo.

16. 2,2-Dimethyl-8-acetyl-8-bromo-12-hydroxyheptadecanoic acid, the compound of claim 13 wherein A is α,α-dimethylethylene, $R^7$ is ethyl and Q is bromo.

17. 3,3-Dimethyl-8-acetyl-8-chloro-12-hydroxyheptadecanoic acid, the compound of claim 13 wherein A is β,β-dimethylethylene, $R^7$ is ethyl, and Q is chloro.

18. The compound of claim 1 which has the formula:

$$CH_3CO-\underset{\underset{\underset{R^1\ \ OH}{/\ \backslash}}{(CH_2)_3-C-(CH_2)_3-R^4}}{\overset{\overset{O}{\|}}{C}}-(CH_2)_4-A-COOY$$

wherein A is ethylene; $R^1$ is methyl or hydrogen; $R^4$ is hydrogen or loweralkyl; Y is alkyl having 1-10 carbon atoms; and Q is chloro or bromo.

19. Methyl 8-acetyl-8-chloro-12-hydroxyheptadecanoate, the compound of claim 18 wherein A is ethylene, R is hydrogen, $R^4$ is ethyl, Y is methyl, and Q is chloro.

* * * * *